(12) United States Patent
Ranade et al.

(10) Patent No.: US 8,067,026 B2
(45) Date of Patent: Nov. 29, 2011

(54) DRUG RELEASE REGIONS FOR MEDICAL DEVICES, WHICH INCLUDE POLYCYCLIC-STRUCTURE-CONTAINING POLYMERS

(75) Inventors: Shrirang V. Ranade, Arlington, MA (US); Michael N. Helmus, Worcester, MA (US); Robert E. Richard, Wrentham, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1727 days.

(21) Appl. No.: 11/079,621

(22) Filed: Mar. 14, 2005

(65) Prior Publication Data

US 2006/0204545 A1 Sep. 14, 2006

(51) Int. Cl.
*A61F 2/02* (2006.01)
*A61F 13/00* (2006.01)
*A61F 2/00* (2006.01)
*A61F 2/01* (2006.01)
*A61F 2/24* (2006.01)

(52) U.S. Cl. .................. 424/425; 424/422; 424/423
(58) Field of Classification Search .................. 424/425, 424/422, 423
See application file for complete search history.

(56) References Cited

U.S. PATENT DOCUMENTS

| | | | | |
|---|---|---|---|---|
| 5,733,925 | A | 3/1998 | Kunz et al. | 514/449 |
| 6,545,097 | B2 | 4/2003 | Pinchuk et al. | 525/240 |
| 2003/0235603 | A1 | 12/2003 | Schwarz et al. | 424/426 |
| 2004/0106953 | A1* | 6/2004 | Yomtov et al. | 607/3 |
| 2004/0202691 | A1* | 10/2004 | Richard | 424/423 |
| 2005/0025802 | A1 | 2/2005 | Richard et al. | 424/423 |
| 2005/0027283 | A1 | 2/2005 | Richard et al. | 604/890.1 |

FOREIGN PATENT DOCUMENTS

| | | |
|---|---|---|
| WO | WO 02/16463 A2 | 2/2002 |
| WO | WO 04/000267 A1 | 12/2003 |
| WO | WO 2005/011769 A2 | 2/2005 |
| WO | WO2005001239 * | 10/2005 |

OTHER PUBLICATIONS

Budd, Peter M. et al., "Free volume and intrinsic microporosity in polymers," *Journal of Materials Chemistry*, vol. 15 (2005): 1977-1986.
Budd, Peter M., et al., "Polymers of intrinsic micoporosity (PIMs): robust, solution-processable, organic nanoporous materials," *Chemical Communications*, 2004, pp. 230-231.
Budd, Peter M., et al., "Microporous polymeric materials," *Materials Today*, Apr. 2004, pp. 40-46.
Amara, John P., "Incorporation of Internal Free Volume: Synthesis and Characterization of Iptycene-Elaborated Poly(butadiene)s," *Macromolecules*, 2004, 37(8) pp. 3068-3070.
Li, Hailian, et al., "Design and synthesis of an exceptionally stable and highly porous metal-organic framework," *Nature*, vol. 402, Nov. 18, 1999, pp. 276-279.
"Introducing intrinsic porosity to polymers," *Materials Today*, Jan. 2004, p. 12.
Pyun, Jeffrey et al., "Synthesis of Nanocomposite Organic/Inorganic Hybrid Materials Using Controlled/ "Living" Radical Polymerization," *Chem. Mater.* 2001, vol. 13, pp. 3436-3448.

* cited by examiner

*Primary Examiner* — Jason M Sims
*Assistant Examiner* — Zohreh Vakili
(74) *Attorney, Agent, or Firm* — Mayer & Williams PC; David B. Bonham; Keum J. Park

(57) ABSTRACT

According to an aspect of the present invention, implantable or insertable medical devices are provided, which contain polymeric release regions that control the release of one or more therapeutic agents. The polymeric release regions, in turn, contain one or more polymers that contain one or more rigid, nonplanar polycyclic molecular structures. The therapeutic agent is disposed beneath or within the polymeric release region.

32 Claims, No Drawings

DRUG RELEASE REGIONS FOR MEDICAL DEVICES, WHICH INCLUDE POLYCYCLIC-STRUCTURE-CONTAINING POLYMERS

FIELD OF THE INVENTION

The present invention relates generally to medical devices, and more particularly to implantable or insertable medical devices which contain polymeric regions for release of therapeutic agents.

BACKGROUND OF THE INVENTION

The in vivo delivery of a biologically active agent within the body of a patient is common in the practice of modern medicine. In vivo delivery of biologically active agents is often implemented using medical devices that may be temporarily or permanently placed at a target site within the body. These medical devices can be maintained, as required, at their target sites for short or prolonged periods of time, delivering biologically active agents at the target site.

For example, numerous polymer-based medical devices have been developed for the delivery of therapeutic agents to the body. Examples include drug eluting coronary stents, which are commercially available from Boston Scientific Corp. (TAXUS), Johnson & Johnson (CYPHER), and others.

In accordance with typical delivery strategies, a therapeutic agent is provided within or beneath a biostable or biodisintegrable polymeric layer that is associated with a medical device. Once the medical device is placed at the desired location within a patient, the therapeutic agent is released from the medical device with a profile that is dependent, for example, upon the loading of the therapeutic agent and upon the nature of the polymeric layer.

Controlling the rate of therapeutic agent release and the overall dose are key parameters for proper treatment in many cases. Selection of the polymeric layer will have a great impact on these parameters.

SUMMARY OF THE INVENTION

According to an aspect of the present invention, implantable or insertable medical devices are provided, which contain polymeric release regions that control the release of one or more therapeutic agents. The polymeric release regions, in turn, contain one or more polycyclic-structure-containing polymers that contain one or more rigid, nonplanar polycyclic molecular structures. The therapeutic agent is disposed beneath or within the polymeric release region.

An advantage of the present invention is that polymeric release regions can be provided which provide for enhanced storage and/or release of therapeutic agents.

These and other aspects, embodiments and advantages of the present invention will become immediately apparent to those of ordinary skill in the art upon review of the Detailed Description and Claims to follow.

DETAILED DESCRIPTION OF THE INVENTION

A more complete understanding of the present invention is available by reference to the following detailed description of numerous aspects and embodiments of the invention. The detailed description of the invention which follows is intended to illustrate but not limit the invention. The scope of the invention is defined by the appended claims.

In one aspect, the present invention provides implantable or insertable medical devices, which contain polymeric release regions that control the release of one or more therapeutic agents. The polymeric release regions contain one or more polycyclic-structure-containing polymers, which contain one or more rigid, nonplanar polycyclic (i.e., bicyclic, tricyclic, quadracyclic, etc.) molecular structures. A therapeutic agent is disposed beneath or within the polymeric release region.

As used herein a "polymeric release region" is a polymer containing region that controls the release of one or more therapeutic agents, which typically comprises at least 50 wt % polymers, more typically at least 75 wt % polymers.

Medical devices benefiting from the present invention include a wide variety of implantable or insertable medical devices, which are implanted or inserted either for procedural uses or as implants. Examples include catheters (e.g., renal or vascular catheters such as balloon catheters), guide wires, balloons, filters (e.g., vena cava filters), stents (including coronary artery stents, peripheral vascular stents such as cerebral stents, urethral stents, ureteral stents, biliary stents, tracheal stents, gastrointestinal stents and esophageal stents), stent grafts, vascular grafts, vascular access ports, embolization devices including cerebral aneurysm filler coils (including Guglilmi detachable coils and metal coils), myocardial plugs, pacemaker leads, left ventricular assist hearts and pumps, total artificial hearts, heart valves, vascular valves, tissue bulking devices, tissue engineering scaffolds for cartilage, bone, skin and other in vivo tissue regeneration, sutures, suture anchors, anastomosis clips and rings, tissue staples and ligating clips at surgical sites, cannulae, metal wire ligatures, orthopedic prosthesis such as bone grafts, bone plates, joint prostheses, as well as various other medical devices that are adapted for implantation or insertion into the body.

The medical devices of the present invention include implantable and insertable medical devices that are used for systemic treatment, as well as those that are used for the localized treatment of any mammalian tissue or organ. Non-limiting examples are tumors; organs including the heart, coronary and peripheral vascular system (referred to overall as "the vasculature"), the urogenital system, including kidneys, bladder, urethra, ureters, prostate, vagina, uterus and ovaries, eyes, lungs, trachea, esophagus, intestines, stomach, brain, liver and pancreas, skeletal muscle, smooth muscle, breast, dermal tissue, cartilage, tooth and bone.

As used herein, "treatment" refers to the prevention of a disease or condition, the reduction or elimination of symptoms associated with a disease or condition, or the substantial or complete elimination of a disease or condition. Preferred subjects (also referred to as "patients") are vertebrate subjects, more preferably mammalian subjects and more preferably human subjects.

Specific examples of medical devices for use in conjunction with the present invention include vascular stents, such as coronary stents and cerebral stents, which deliver a therapeutic agent into the vasculature for the treatment of restenosis.

In some embodiments, the polymeric release regions of the present invention correspond to an entire medical device. In other embodiments, the polymeric release regions correspond or to one or more portions of a medical device. For instance, the polymeric release regions can be in the form of one or more fibers which are incorporated into a medical device, in the form of one or more polymeric layers formed over all or only a portion of an underlying medical device substrate, and so forth. Layers can be provided over an underlying substrate at a variety of locations, and in a variety of shapes (e.g., in desired patterns, for instance, using appropriate masking techniques, such as lithographic techniques), and they can be formed from a variety of polymeric materials. Materials for use as underlying medical device substrates include ceramic, metallic and polymeric substrates. The substrate material can also be a carbon- or silicon-based material. As used herein a "layer" of a given material is a region of that material whose thickness is small compared to both its length and width. As used herein a layer need not be planar, for example, taking on the contours of an underlying substrate. Layers can be discontinuous (e.g., patterned). Terms such as "film," "layer" and "coating" may be used interchangeably herein.

Release regions in accordance with the present invention include carrier regions and barrier regions. By "carrier region" is meant a release region which further comprises a therapeutic agent and from which the therapeutic agent is released. For example, in some embodiments, the carrier region constitutes the entirety of the medical device (e.g., provided in the form of a stent body). In other embodiments, the carrier region corresponds on only a portion of the device (e.g., a coating overlying a medical device substrate such as a stent body). By "barrier region" is meant a region which is disposed between a source of therapeutic agent and a site of intended release, and which controls the rate at which therapeutic agent is released. For example, in some embodiments, the medical device consists of a barrier region that surrounds a source of therapeutic agent. In other embodiments, the barrier region is disposed over a source of therapeutic agent, which is in turn disposed over all or a portion of a medical device substrate.

The release profile can also be modified by changing the chemical composition, size, number and/or position of the polymeric release regions within the device, among other parameters. For example, the release profile of polymeric carrier and barrier layers in accordance with the presenting invention can be modified by varying the thickness or surface areas of the same. Moreover, multiple polymeric release regions can be employed to modify the release profile. For example, multiple carrier or barrier layers of the invention, either having the same or different content (e.g., different polymeric and/or therapeutic agent content), can be stacked on top of one another, can be positioned laterally to one another, and so forth.

As a specific example, for tubular devices such as stents (which can comprise, for example, a laser or mechanically cut tube, one or more braided, woven, or knitted filaments, etc.), polymeric release layers can be provided on the luminal surfaces, on the abluminal surfaces, on the lateral surfaces between the luminal and abluminal surfaces (including the ends), patterned along the luminal or abluminal length of the devices, and so forth. Moreover, release layers can control the release of the same or differing underlying biologically active agent. It is therefore possible, for example, to release the same or different therapeutic agents at different rates from different locations on the medical device. As another specific example, it is possible to provide a tubular medical device (e.g., a vascular stent) having a release layer which contains or is disposed over a first biologically active agent (e.g., an antithrombotic agent) at its inner, luminal surface and a second release layer which contains or is disposed over a second biologically active agent that differs from the first biologically active agent (e.g., an antiproliferative agent) at its outer, abluminal surface (as well as on the ends, if desired).

As indicated above, in one aspect, the present invention provides implantable or insertable medical devices, which contain polymeric release regions that regulate the release of one or more therapeutic agents. The polymeric release regions contain one or more polycyclic-structure-containing polymers, which contain one or more rigid, nonplanar polycyclic (e.g., bicyclic, tricyclic, etc.) molecular structures. For example, in some embodiments of the invention, the polycyclic-structure-containing polymers contain one or more polymer chains with a rigid non-planar polycyclic backbone structure. As another example, in some embodiments, the polycyclic-structure-containing polymers contain one or more polymer chains which have a plurality of pendant rigid non-planar polycyclic structures.

As used herein, "polymers" are molecules that contain one or more chains, each containing multiple copies of the same or differing constitutional units, commonly referred to as monomers. An example of a common polymer chain is polystyrene

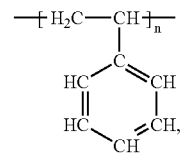

where n is an integer of 10 or more, more typically on the order of 10's, 100's, 1000's or even more, in which the chain contains styrene monomers:

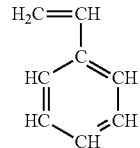

(i.e., the chain originates from, or has the appearance of originating from, the polymerization of styrene monomers, in this case, the addition polymerization of styrene monomers).

Polymers for use in the polymeric release regions of the present invention can have a variety of architectures, including cyclic, linear and branched architectures. Branched architectures include star-shaped architectures (e.g., architectures in which three or more chains emanate from a single branch point), comb architectures (e.g., architectures having a main chain and a plurality of side chains) and dendritic architectures (e.g., arborescent and hyperbranched polymers), among others.

The polymers for use in the polymeric release regions of the present invention can contain, for example, homopolymer chains, which contain multiple copies of a single constitutional unit, and/or copolymer chains, which contain multiple copies of at least two dissimilar constitutional units, which units may be present in any of a variety of distributions including random, statistical, gradient and periodic (e.g., alternating) distributions. Polymers containing two or more differing homopolymer or copolymer chains are referred to herein as "block copolymers."

Without wishing to be bound by theory of operation, it is believed that polymers containing one or more rigid, nonplanar polycyclic molecular structures are capable of providing internal free volume to the release regions of the invention. For a discussion of internal free volume, see, e.g., J. P. Amara and T, M. Swager, "Incorporation of Internal Free Volume: Synthesis and Characterization of Iptycene-Elaborated Poly (butadiene)s," *Macromolecules;* 2004; 37(8) pp 3068-3070 (hereinafter Amara and Swager). This internal free volume, in turn, provides space which may be occupied by the therapeutic agent and which can enhance storage of the therapeutic agent (e.g., in the case of a carrier region) and/or the ability of the therapeutic agent to diffuse into, through, and/or out of the release region (e.g., in the case of a barrier region or carrier region).

Moreover, in some instances, polymers containing nonplanar polycyclic molecular structures are intrinsically porous, providing polymeric regions with near-molecular-sized pores, for example, pore sizes of less than 2 nm, beneficially 0.2 to 2 nm, and more beneficially 0.4 to 0.8 nm. For a discussion of microporous polymers see, e.g., P. M. Budd, et al., "Polymers of intrinsic microporosity (PIMs): robust, solution-processable, organic nanoporous materials," *Chemical Communications,* 2004, 230-231 (hereinafter Budd et al.). The polymers are intrinsically microporous, for example, due to the fact that the rigid polycyclic structures, while commonly having planar portions, are not planar overall, and therefore cannot flex or stack upon one another as required for efficient packing. In other words, the polymers may form porous solids, because their structures cannot fill space efficiently. Id. These pores provide space which may be occupied by the therapeutic agent and which may further enhance the ability of the release region to store and/or to promote diffusion of the therapeutic agent. Such pores are also interconnected in some cases, further facilitating transport of the therapeutic agent within the release region.

As noted above, in some embodiments, the polymeric release regions of the invention are provided with polycyclic-structure-containing polymers that contain one or more polymer chains with a rigid non-planar polycyclic backbone structure. Such polymers can be formed, for example, by linking together rigid cyclic (i.e., monocyclic, bicyclic, tricyclic, etc.) monomers via multiple (i.e., two or more) covalent linkages.

For example, polymer synthesis techniques are known by which the rings of multifunctional cyclic monomers can be fused to one another by means of two —O— linkages. See, e.g., Budd et al. Examples of such monomers include the following: (a) polycyclic monomers that have a rigid nonplanar polycyclic structure, such as (i)

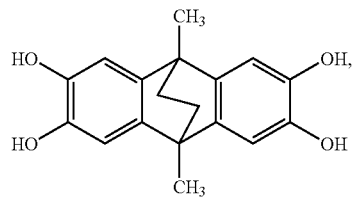

whose structure is perhaps better represented by (ii)

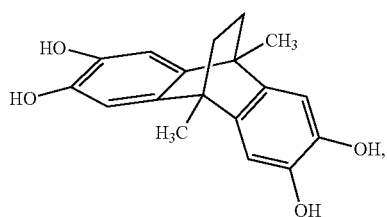

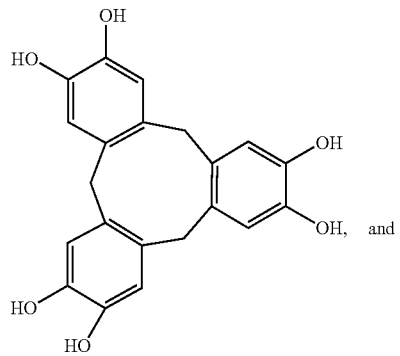

(iii)

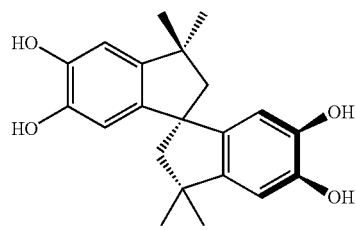

and (b) polycyclic monomers having two cyclic (i.e., monocyclic, bicyclic, tricyclic, etc.) structures that are attached by a single covalent bond, but around which bond rotation between the cyclic structures is hindered, such as (i)

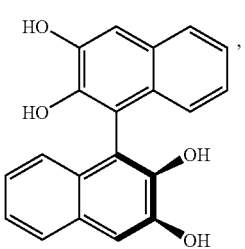

(ii)

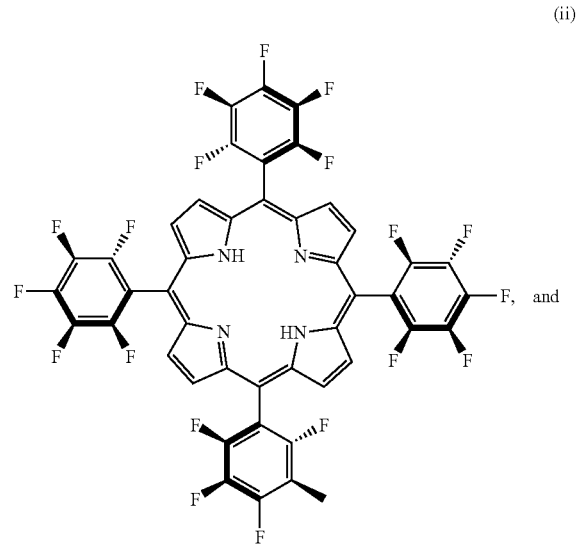

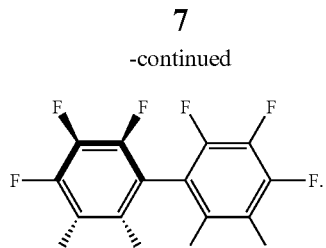

Such structures can be linked, for example, to one another or to similar non-planar structures, or they may be linked to planar structures such as

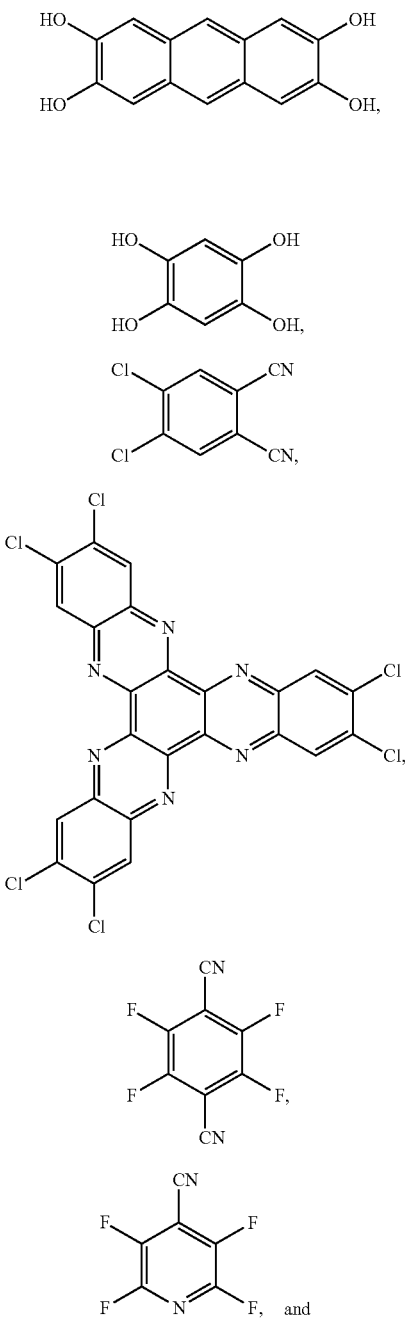

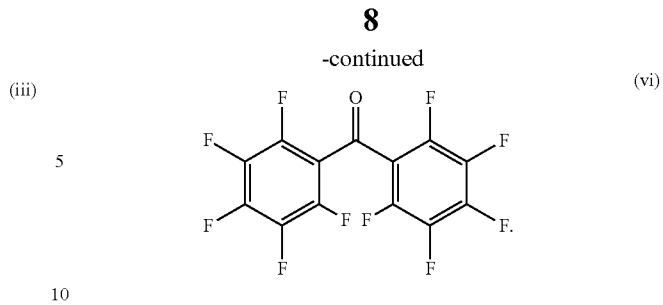

A specific example in which monomers of this type are polymerized is as follows:

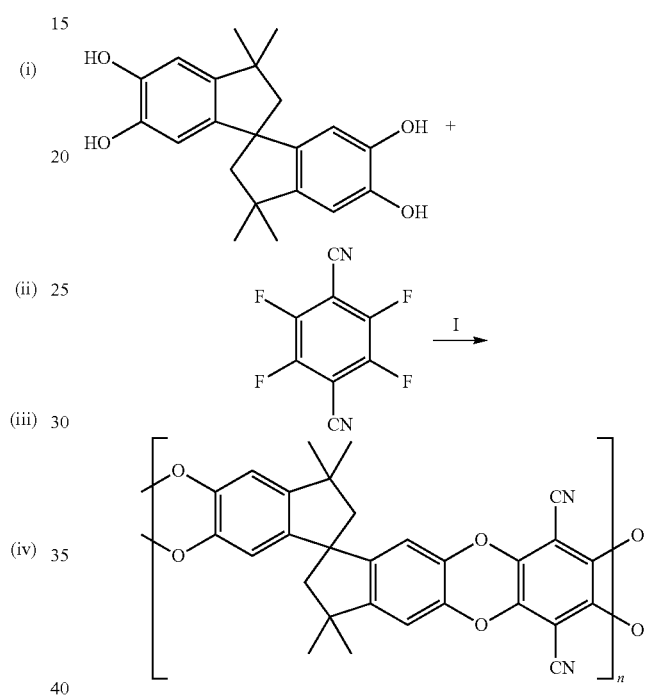

where i=$K_2CO_3$, DMF, 50-70° C. Budd et al. have reported that a significant proportion of the pores of this polymer are micropores (i.e., <2 nm) having dimensions in the 0.4-0.8 nm range, with evidence of some mesoporosity (i.e., pore sizes within the 2-50 nm range). Total pore volume and surface area are estimated at 0.78 $cm^3/g$ and 850 $m^2/g$, respectively. As indicated above, pores can enhance the storage of therapeutic agent within the release regions of the invention as well as the transport of therapeutic agent, into, out of and/or through the release regions.

In some embodiments, it is desirable to provide the polymeric regions of the present invention with additional polymer chains other than those that contain rigid, nonplanar polycyclic molecular structures. For example, such additional polymer chains can be attached to chains containing the rigid, nonplanar polycyclic molecular structures (e.g., forming a block copolymer, which has one or more blocks containing rigid, nonplanar polycyclic molecular structures and one or more additional blocks, which do not), or release regions can be provided with additional polymer chains by simply blending a polymer containing the rigid, nonplanar polycyclic molecular structures with an additional polymer that does not.

Examples of such additional polymer chains include a wide variety of homopolymers and copolymers (including alternating, random, statistical, gradient and block copolymers), which may be cyclic, linear or branched (e.g., the polymers may have star, comb or dendritic architecture), which may be natural or synthetic, and which may be thermoplastic or thermosetting. Specific polymers for use as such additional polymer chains may be selected, for example, from the following: polycarboxylic acid polymers and copolymers including polyacrylic acids; acetal polymers and copolymers; acrylate and methacrylate polymers and copolymers (e.g., n-butyl methacrylate); cellulosic polymers and copolymers, including cellulose acetates, cellulose nitrates, cellulose propionates, cellulose acetate butyrates, cellophanes, rayons, rayon triacetates, and cellulose ethers such as carboxymethyl celluloses and hydroxyalkyl celluloses; polyoxymethylene polymers and copolymers; polyimide polymers and copolymers such as polyether block imides and polyether block amides, polyamidimides, polyesterimides, and polyetherimides; polysulfone polymers and copolymers including polyarylsulfones and polyethersulfones; polyamide polymers and copolymers including nylon 6,6, nylon 12, polycaprolactams and polyacrylamides; resins including alkyd resins, phenolic resins, urea resins, melamine resins, epoxy resins, allyl resins and epoxide resins; polycarbonates; polyacrylonitriles; polyvinylpyrrolidones (cross-linked and otherwise); polymers and copolymers of vinyl monomers including polyvinyl alcohols, polyvinyl halides such as polyvinyl chlorides, ethylene-vinyl acetate copolymers (EVA), polyvinylidene chlorides, polyvinyl ethers such as polyvinyl methyl ethers, polystyrenes, styrene-maleic anhydride copolymers, vinyl-aromatic-olefin copolymers, including styrene-butadiene copolymers, styrene-ethylene-butylene copolymers (e.g., a polystyrene-polyethylene/butylene-polystyrene (SEBS) copolymer, available as Kraton® G series polymers), styrene-isoprene copolymers (e.g., polystyrene-polyisoprene-polystyrene), acrylonitrile-styrene copolymers, acrylonitrile-butadiene-styrene copolymers, styrene-butadiene copolymers and styrene-isobutylene copolymers (e.g., polyisobutylene-polystyrene and polystyrene-polyisobutylene-polystyrene block copolymers such as those disclosed in U.S. Pat. No. 6,545,097 to Pinchuk), polyvinyl ketones, polyvinylcarbazoles, and polyvinyl esters such as polyvinyl acetates; polybenzimidazoles; ethylene-methacrylic acid copolymers and ethylene-acrylic acid copolymers, where some of the acid groups can be neutralized with either zinc or sodium ions (commonly known as ionomers); polyalkyl oxide polymers and copolymers including polyethylene oxides (PEO); polyesters including polyethylene terephthalates and aliphatic polyesters such as polymers and copolymers of lactide (which includes lactic acid as well as d-, l- and meso lactide), epsilon-caprolactone, glycolide (including glycolic acid), hydroxybutyrate, hydroxyvalerate, para-dioxanone, trimethylene carbonate (and its alkyl derivatives), 1,4-dioxepan-2-one, 1,5-dioxepan-2-one, and 6,6-dimethyl-1,4-dioxan-2-one (a copolymer of poly(lactic acid) and poly(caprolactone) is one specific example); polyether polymers and copolymers including polyarylethers such as polyphenylene ethers, polyether ketones, polyether ether ketones; polyphenylene sulfides; polyisocyanates; polyolefin polymers and copolymers, including polyalkylenes such as polypropylenes, polyethylenes (low and high density, low and high molecular weight), polybutylenes (such as polybut-1-ene and polyisobutylene), polyolefin elastomers (e.g., santoprene), ethylene propylene diene monomer (EPDM) rubbers, poly-4-methyl-pen-1-enes, ethylene-alpha-olefin copolymers, ethylene-methyl methacrylate copolymers and ethylene-vinyl acetate copolymers; fluorinated polymers and copolymers, including polytetrafluoroethylenes (PTFE), poly(tetrafluoroethylene-co-hexafluoropropene) (FEP), modified ethylene-tetrafluoroethylene copolymers (ETFE), and polyvinylidene fluorides (PVDF); silicone polymers and copolymers; thermoplastic polyurethanes (TPU); elastomers such as elastomeric polyurethanes and polyurethane copolymers (including block and random copolymers that are polyether based, polyester based, polycarbonate based, aliphatic based, aromatic based and mixtures thereof; examples of commercially available polyurethane copolymers include Bionate®, Carbothane®, Tecoflex®, Tecothane®, Tecophilic®, Tecoplast®, Pellethane®, Chronothane® and Chronoflex®); p-xylylene polymers; polyiminocarbonates; copoly(ether-esters) such as polyethylene oxide-polylactic acid copolymers; polyphosphazines; polyalkylene oxalates; polyoxaamides and polyoxaesters (including those containing amines and/or amido groups); polyorthoesters; biopolymers, such as polypeptides, proteins, polysaccharides and fatty acids (and esters thereof), including fibrin, fibrinogen, collagen, elastin, chitosan, gelatin, starch, glycosaminoglycans such as hyaluronic acid; as well as blends and further copolymers of the above.

The additional polymer chains can be provided for various reasons. For instance, additional chains may be introduced (a) to render the release region more hydrophilic (or more hydrophobic), (b) to modulate the release profile of the therapeutic agent, (c) to affect the mechanical characteristic of the material, and so forth.

As a specific example, polymer chains with rigid non-planar polycyclic backbone structures presented above, for instance,

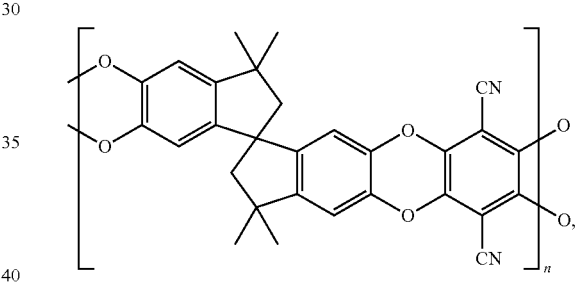

have been shown to have a very high glass transition temperature ($T_g$), where $T_g$ can be measured by any of a number of techniques including differential scanning calorimetry (DSC), dynamic mechanical analysis (DMA), or dielectric analysis (DEA). In fact, for this particular polymer, no glass transition (or melting point) was observed prior to thermal decomposition. Consequently, it is desirable in certain embodiments of the invention to introduce one or more polymer chains into the release region which have glass transition temperatures that are below ambient temperature ("low $T_g$ chains"), more typically below 25° C., below 0° C., below −25° C., or even below −50° C. "Ambient temperature" is body temperature (e.g., 35° C.-40° C.). As a result of their low glass transition temperatures, low $T_g$ polymer chains are typically elastomeric at ambient temperature, although some low $T_g$ polymer blocks, such as silicone (e.g. polydimethylsiloxane), are viscous liquids or millable gums at room temperature. As specific examples, such low $T_g$ chains can be attached to the high $T_g$ polycyclic-structure-containing polymers (e.g., by forming block copolymers having one or more rigid polycyclic-structure-containing blocks and one or more flexible blocks), or a polymer having one or more low $T_g$ chains can be simply added to the polycyclic-structure-containing polymers to form polymer blends.

Polymeric regions having both low and high $T_g$ polymer chains are known to possess many interesting physical properties due to the presence of the low $T_g$ phase, which is soft and elastomeric at body temperature, and the high $T_g$ phase, which is hard at this temperature. As a specific example, block copolymers of polyisobutylene and polystyrene, for example, polystyrene-polyisobutylene-polystyrene triblock copolymers (SIBS copolymers), described in U.S. Pat. No. 6,545,097 to Pinchuk et al., which is hereby incorporated by reference in its entirety, have proven valuable as release polymers in implantable or insertable drug-releasing medical devices. These copolymers are particularly useful for medical device applications because of their excellent strength, biostability and biocompatibility, particularly within the vasculature. For example, these copolymers exhibit high tensile strength, which frequently ranges from 2,000 to 4,000 psi or more, and resist cracking and other forms of degradation under typical in vivo conditions.

As previously noted, various embodiments of the invention employ polymers which contain one or more polymer chains that have a plurality of pendant rigid non-planar polycyclic structures. Specific examples of such polycyclic-structure-containing polymers are described in Amara and Swager, and are made from monomers that polymerize in a fashion akin to the polymerization of butadiene

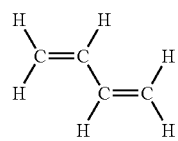

to form polybutadiene

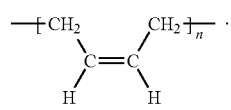

For instance,

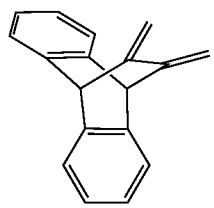

has been shown to polymerize into

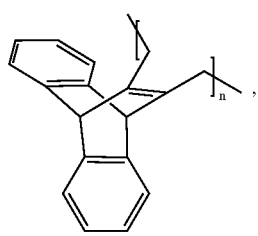

while

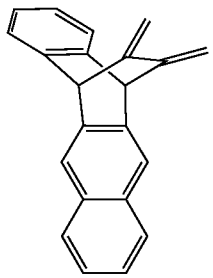

has been shown to polymerize into

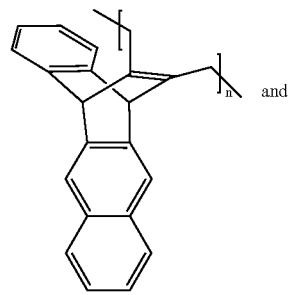 and

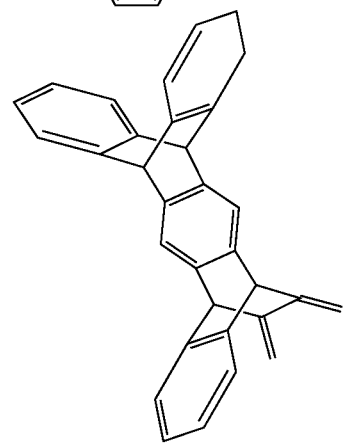

has been shown to polymerize into

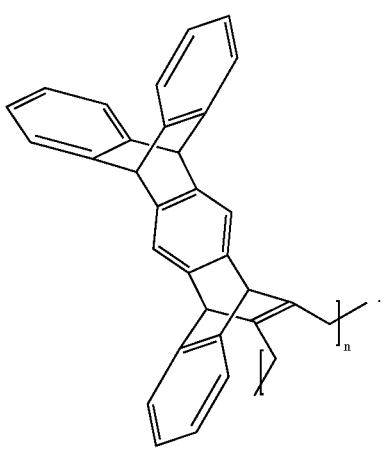

Such polymers have significant internal free volume, and they are high $T_g$ polymers, which display $T_g$'s ranging from 145 to 233° C.

As above, these polymers can be used alone to form release regions in accordance with the present invention, or they can be combined with additional polymer chains (e.g., by covalently linking the additional polymer chains thereby forming block copolymers, or by blending the additional polymer chains).

Moreover, polymers for use in the release regions of the invention can be formed by copolymerizing one or more monomers having a rigid non-planar polycyclic structure and one or more monomers that do not. For example, the monomers illustrated immediately above have terminal unsaturation, rendering them readily copolymerizable with various other unsaturated monomers using a variety of polymerization methods, including anionic, cationic and radical polymerization methods, such as azobis(isobutyronitrile)- or peroxide-initiated polymerizations and controlled/"living" radical polymerizations such as metal-catalyzed atom transfer radical polymerization (ATRP), stable free-radical polymerization (SFRP), nitroxide-mediated processes (NMP), and degenerative transfer (e.g., reversible addition-fragmentation chain transfer (RAFT)) processes, among others. These methods are well-detailed in the literature and are described, for example, in an article by Pyun and Matyjaszewski, "Synthesis of Nanocomposite Organic/Inorganic Hybrid Materials Using Controlled/"Living" Radical Polymerization," *Chem. Mater.*, 13:3436-3448 (2001), the contents of which are incorporated by reference in its entirety.

Monomers that are suitable for copolymerization with monomers containing rigid, nonplanar polycyclic molecular structures, can be selected from those set forth below. The monomers described below are organized according to the published glass transition temperature ($T_g$) of the corresponding homopolymer, although other organizational schemes could, of course, have been employed.

Monomers that display a low $T_g$ when homopolymerized (also referred to herein as "low $T_g$ monomers") include acrylic monomers, methacrylic monomers, vinyl ether monomers, cyclic ether monomers, ester monomers, unsaturated hydrocarbon monomers (including alkene monomers), halogenated unsaturated hydrocarbon monomers (including halogenated alkene monomers), and siloxane monomers. Numerous specific examples are listed below.

Specific acrylic monomers include, for example, (a) alkyl acrylates such as methyl acrylate ($T_g$ 10° C.), ethyl acrylate ($T_g$ -24° C.), propyl acrylate, isopropyl acrylate ($T_g$ -11°° C., isotactic), butyl acrylate ($T_g$ -54° C.), sec-butyl acrylate ($T_g$ -26° C.), isobutyl acrylate ($T_g$ -24° C.), cyclohexyl acrylate ($T_g$ 19° C.), 2-ethylhexyl acrylate ($T_g$ -50° C.), dodecyl acrylate ($T_g$ -3° C.) and hexadecyl acrylate ($T_g$ 35° C.), (b) arylalkyl acrylates such as benzyl acrylate ($T_g$ 6° C.), (c) alkoxyalkyl acrylates such as 2-ethoxyethyl acrylate ($T_g$ -50° C.) and 2-methoxyethyl acrylate ($T_g$ -50° C.), (d) halo-alkyl acrylates such as 2,2,2-trifluoroethyl acrylate ($T_g$ -10° C.) and (e) cyano-alkyl acrylates such as 2-cyanoethyl acrylate ($T_g$ 4° C.).

Specific methacrylic monomers include, for example, (a) alkyl methacrylates such as butyl methacrylate ($T_g$ 20° C.), hexyl methacrylate ($T_g$ -5° C.), 2-ethylhexyl methacrylate ($T_g$ -10° C.), octyl methacrylate ($T_g$ -20° C.), dodecyl methacrylate ($T_g$ -65° C.), hexadecyl methacrylate ($T_g$ 15° C.) and octadecyl methacrylate ($T_g$ -100° C.) and (b) aminoalkyl methacrylates such as diethylaminoethyl methacrylate ($T_g$ 20° C.) and 2-tert-butyl-aminoethyl methacrylate ($T_g$ 33° C.).

Specific vinyl ether monomers include for example, (a) alkyl vinyl ethers such as methyl vinyl ether ($T_g$ -31° C.), ethyl vinyl ether ($T_g$ -43° C.), propyl vinyl ether ($T_g$ -49° C.), butyl vinyl ether ($T_g$ -55° C.), isobutyl vinyl ether ($T_g$ -19° C.), 2-ethylhexyl vinyl ether ($T_g$ -66° C.) and dodecyl vinyl ether ($T_g$ -62° C.).

Specific cyclic ether monomers include for example, tetrahydrofuran ($T_g$ -84° C.), trimethylene oxide ($T_g$ -78° C.), ethylene oxide ($T_g$ -66° C.), propylene oxide ($T_g$ -75° C.), methyl glycidyl ether ($T_g$ -62° C.), butyl glycidyl ether ($T_g$ -79° C.), allyl glycidyl ether ($T_g$ -78° C.), epibromohydrin ($T_g$ -14° C.), epichlorohydrin ($T_g$ -22° C.), 1,2-epoxybutane ($T_g$ -70° C.), 1,2-epoxyoctane ($T_g$ -67° C.) and 1,2-epoxydecane ($T_g$ -70° C.).

Specific ester monomers (other than acrylates and methacrylate esters) include for example, ethylene malonate ($T_g$ -29° C.), vinyl acetate ($T_g$ 30° C.), and vinyl propionate ($T_g$ 10° C.).

Specific alkene monomers include, for example, ethylene, propylene ($T_g$ -8 to -13° C.), isobutylene ($T_g$ -73° C.), 1-butene ($T_g$ -24° C.), trans-butadiene ($T_g$ -58° C.), 4-methyl pentene ($T_g$ 29° C.), 1-octene ($T_g$ -63° C.) and other α-olefins, cis-isoprene ($T_g$ -63° C.), and trans-isoprene ($T_g$ -66° C.).

Specific halogenated alkene monomers include vinylidene chloride ($T_g$ -18° C.), vinylidene fluoride ($T_g$ -40° C.), cis-chlorobutadiene ($T_g$ -20° C.), and trans-chlorobutadiene ($T_g$ -40° C.).

Specific siloxane monomers include, for example, dimethylsiloxane ($T_g$ -127° C.), diethylsiloxane, methylethylsiloxane, methylphenylsiloxane ($T_g$ -86° C.), and diphenylsiloxane.

Monomers that display a high $T_g$ when homopolymerized (also referred to herein as "high $T_g$ monomers") include: vinyl aromatic monomers, other vinyl monomers (besides vinyl aromatic monomers), other aromatic monomers (besides vinyl aromatic monomers), methacrylic monomers, and acrylic monomers. Elevated or high $T_g$ polymer chains are those that display at least one glass transition temperature that is above ambient temperature, more typically above 50° C., above 75° C., or even above 100° C.

Vinyl aromatic monomers are those having aromatic and vinyl moieties and include, for example, unsubstituted monomers, vinyl-substituted monomers and ring-substituted monomers. Specific vinyl aromatic monomers include the following: (a) unsubstituted vinyl aromatics, such as atactic styrene ($T_g$ 100° C.), isotactic styrene ($T_g$ 100° C.) and 2-vinyl naphthalene ($T_g$ 151° C.), (b) vinyl substituted aromatics such as α-methyl styrene, (c) ring-substituted vinyl aromatics including (i) ring-alkylated vinyl aromatics such as 3-methylstyrene ($T_g$ 97° C.), 4-methylstyrene ($T_g$ 97° C.), 2,4-dimethylstyrene ($T_g$ 112° C.), 2,5-dimethylstyrene ($T_g$ 143° C.), 3,5-dimethylstyrene ($T_g$ 104° C.), 2,4,6-trimethylstyrene ($T_g$ 162° C.), and 4-tert-butylstyrene ($T_g$ 127° C.), (ii) ring-alkoxylated vinyl aromatics, such as 4-methoxystyrene ($T_g$ 113° C.) and 4-ethoxystyrene ($T_g$ 86° C.), (iii) ring-halogenated vinyl aromatics such as 2-chlorostyrene ($T_g$ 119° C.), 3-chlorostyrene ($T_g$ 90° C.), 4-chlorostyrene ($T_g$ 110° C.), 2,6-dichlorostyrene ($T_g$ 167° C.), 4-bromostyrene ($T_g$ 118° C.) and 4-fluorostyrene ($T_g$ 95° C.) and (iv) ester-substituted vinyl aromatics such as 4-acetoxystyrene ($T_g$ 116° C.).

Specific other vinyl monomers include the following: (a) vinyl alcohol ($T_g$ 85° C.); (b) vinyl esters such as vinyl benzoate ($T_g$ 71° C.), vinyl 4-tert-butyl benzoate ($T_g$ 101° C.), vinyl cyclohexanoate ($T_g$ 76° C.), vinyl pivalate ($T_g$ 86° C.), vinyl trifluoroacetate ($T_g$ 46° C.), vinyl butyral ($T_g$ 49° C.), (c) vinyl amines such as 2-vinyl pyridine ($T_g$ 104° C.), 4-vinyl pyridine ($T_g$ 142° C.), and vinyl carbazole ($T_g$ 227° C.), (d) vinyl halides such as vinyl chloride ($T_g$ 81° C.) and vinyl fluoride ($T_g$ 40° C.); (e) alkyl vinyl ethers such as tert-butyl vinyl ether ($T_g$ 88° C.) and cyclohexyl vinyl ether ($T_g$ 81° C.), and (f) other vinyl compounds such as 1-vinyl-2-pyrrolidone ($T_g$ 54° C.) and vinyl ferrocene ($T_g$ 189° C.).

Specific other aromatic monomers, other than vinyl aromatics, include acenaphthalene ($T_g$ 214° C.) and indene ($T_g$ 85° C.).

Specific methacrylic monomers include (a) methacrylic acid ($T_g$ 228° C.), (b) methacrylic acid salts such as sodium methacrylate ($T_g$ 310° C.), (c) methacrylic acid anhydride ($T_g$ 159° C.), (d) methacrylic acid esters (methacrylates) including (i) alkyl methacrylates such as atactic methyl methacrylate ($T_g$ 105-120° C.), syndiotactic methyl methacrylate ($T_g$ 115° C.), ethyl methacrylate ($T_g$ 65° C.), isopropyl methacrylate ($T_g$ 81° C.), isobutyl methacrylate ($T_g$ 53° C.), t-butyl methacrylate ($T_g$ 118° C.) and cyclohexyl methacrylate ($T_g$ 92° C.), (ii) aromatic methacrylates such as phenyl methacrylate ($T_g$ 110° C.) and including aromatic alkyl methacrylates such as benzyl methacrylate ($T_g$ 54° C.), (iii) hydroxyalkyl methacrylates such as 2-hydroxyethyl methacrylate ($T_g$ 57° C.) and 2-hydroxypropyl methacrylate ($T_g$ 76° C.), (iv) additional methacrylates including isobornyl methacrylate ($T_g$ 110° C.) and trimethylsilyl methacrylate ($T_g$ 68° C.), and (e) other methacrylic-acid derivatives including methacrylonitrile ($T_g$ 120° C.).

Specific acrylic monomers include (a) acrylic acid ($T_g$ 105° C.), its anhydride and salt forms, such as potassium acrylate ($T_g$ 194° C.) and sodium acrylate ($T_g$ 230° C.); (b) certain acrylic acid esters such as tert-butyl acrylate ($T_g$ 43-107° C.), hexyl acrylate ($T_g$ 57° C.) and isobornyl acrylate ($T_g$ 94° C.); (c) acrylic acid amides such as acrylamide ($T_g$ 165° C.), N-isopropylacrylamide ($T_g$ 85-130° C.) and N,N dimethylacrylamide ($T_g$ 89° C.); and (d) other acrylic-acid derivatives including acrylonitrile ($T_g$ 125° C.).

The above monomers can also be used to form homopolymers and copolymers for blending with, or attachment to, the polycyclic-structure-containing polymers, in accordance with various embodiments of the invention.

As noted above, the medical devices of the present invention contain one or more therapeutic agents. "Therapeutic agents," "drugs," "pharmaceutically active agents," "pharmaceutically active materials," and other related terms may be used interchangeably herein. These terms include genetic therapeutic agents, non-genetic therapeutic agents and cells.

Exemplary non-genetic therapeutic agents for use in connection with the present invention include: (a) anti-thrombotic agents such as heparin, heparin derivatives, urokinase, and PPack (dextrophenylalanine proline arginine chloromethylketone); (b) anti-inflammatory agents such as dexamethasone, prednisolone, corticosterone, budesonide, estrogen, sulfasalazine and mesalamine; (c) antineoplastic/antiproliferative/anti-miotic agents such as paclitaxel, 5-fluorouracil, cisplatin, vinblastine, vincristine, epothilones, endostatin, angiostatin, angiopeptin, monoclonal antibodies capable of blocking smooth muscle cell proliferation, and thymidine kinase inhibitors; (d) anesthetic agents such as lidocaine, bupivacaine and ropivacaine; (e) anti-coagulants such as D-Phe-Pro-Arg chloromethyl ketone, an RGD peptide-containing compound, heparin, hirudin, antithrombin compounds, platelet receptor antagonists, anti-thrombin antibodies, anti-platelet receptor antibodies, aspirin, prostaglandin inhibitors, platelet inhibitors and tick antiplatelet peptides; (f) vascular cell growth promoters such as growth factors, transcriptional activators, and translational promotors; (g) vascular cell growth inhibitors such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin; (h) protein kinase and tyrosine kinase inhibitors (e.g., tyrphostins, genistein, quinoxalines); (i) prostacyclin analogs; (j) cholesterol-lowering agents; (k) angiopoietins; (l) antimicrobial agents such as triclosan, cephalosporins, aminoglycosides and nitrofurantoin; (m) cytotoxic agents, cytostatic agents and cell proliferation affectors; (n) vasodilating agents; (o) agents that interfere with endogenous vasoactive mechanisms; (p) inhibitors of leukocyte recruitment, such as monoclonal antibodies; (q) cytokines; (r) hormones; (s) inhibitors of HSP 90 protein (i.e., Heat Shock Protein, which is a molecular chaperone or housekeeping protein and is needed for the stability and function of other client proteins/signal transduction proteins responsible for growth and survival of cells) including geldanamycin, (t) beta-blockers, (u) bARKct inhibitors, (v) phospholamban inhibitors, and (w) Serca 2 gene/protein.

Preferred non-genetic therapeutic agents include paclitaxel, sirolimus, everolimus, tacrolimus, Epo D, dexamethasone, estradiol, halofuginone, cilostazole, geldanamycin, ABT-578 (Abbott Laboratories), trapidil, liprostin, Actinomcin D, Resten-NG, Ap-17, abciximab, clopidogrel, Ridogrel, beta-blockers, bARKct inhibitors, phospholamban inhibitors, and Serca 2 gene/protein among others.

Exemplary genetic therapeutic agents for use in connection with the present invention include anti-sense DNA and RNA as well as DNA coding for the various proteins (as well as the proteins themselves): (a) anti-sense RNA, (b) tRNA or rRNA to replace defective or deficient endogenous molecules, (c) angiogenic and other factors including growth factors such as acidic and basic fibroblast growth factors, vascular endothelial growth factor, endothelial mitogenic growth factors, epidermal growth factor, transforming growth factor α and β, platelet-derived endothelial growth factor, platelet-derived growth factor, tumor necrosis factor α, hepatocyte growth factor and insulin-like growth factor, (d) cell cycle inhibitors including CD inhibitors, and (e) thymidine kinase ("TK") and other agents useful for interfering with cell proliferation. Also of interest is DNA encoding for the family of bone morphogenic proteins ("BMP's"), including BMP-2, BMP-3, BMP-4, BMP-5, BMP-6 (Vgr-1), BMP-7 (OP-1), BMP-8, BMP-9, BMP-10, BMP-11, BMP-12, BMP-13, BMP-14, BMP-15, and BMP-16. Currently preferred BMP's are any of BMP-2, BMP-3, BMP-4, BMP-5, BMP-6 and BMP-7. These dimeric proteins can be provided as homodimers, heterodimers, or combinations thereof, alone or together with other molecules. Alternatively, or in addition, molecules capable of inducing an upstream or downstream effect of a BMP can be provided. Such molecules include any of the "hedgehog" proteins, or the DNA's encoding them.

Vectors for delivery of genetic therapeutic agents include viral vectors such as adenoviruses, gutted adenoviruses, adeno-associated virus, retroviruses, alpha virus (Semliki Forest, Sindbis, etc.), lentiviruses, herpes simplex virus, replication competent viruses (e.g., ONYX-015) and hybrid vectors; and non-viral vectors such as artificial chromosomes and mini-chromosomes, plasmid DNA vectors (e.g., pCOR), cationic polymers (e.g., polyethyleneimine, polyethyleneimine (PEI)), graft copolymers (e.g., polyether-PEI and polyethylene oxide-PEI), neutral polymers PVP, SP1017 (SUPRATEK), lipids such as cationic lipids, liposomes, lipoplexes, nanoparticles, or microparticles, with and without targeting sequences such as the protein transduction domain (PTD).

Cells for use in connection with the present invention include cells of human origin (autologous or allogeneic), including whole bone marrow, bone marrow derived mononuclear cells, progenitor cells (e.g., endothelial progenitor cells), stem cells (e.g., mesenchymal, hematopoietic, neuronal), pluripotent stem cells, fibroblasts, myoblasts, satellite cells, pericytes, cardiomyocytes, skeletal myocytes or macrophage, or from an animal, bacterial or fungal source (xenogeneic), which can be genetically engineered, if desired, to deliver proteins of interest.

Numerous therapeutic agents, not necessarily exclusive of those listed above, have been identified as candidates for vascular treatment regimens, for example, as agents targeting restenosis. Such agents are useful for the practice of the present invention and include one or more of the following: (a) Ca-channel blockers including benzothiazapines such as diltiazem and clentiazem, dihydropyridines such as nifedipine, amlodipine and nicardapine, and phenylalkylamines such as verapamil, (b) serotonin pathway modulators including: 5-HT antagonists such as ketanserin and naftidrofuryl, as well as 5-HT uptake inhibitors such as fluoxetine, (c) cyclic nucleotide pathway agents including phosphodiesterase inhibitors such as cilostazole and dipyridamole, adenylate/Guanylate cyclase stimulants such as forskolin, as well as adenosine analogs, (d) catecholamine modulators including α-antagonists such as prazosin and bunazosine, β-antagonists such as propranolol and α/β-antagonists such as labetalol and carvedilol, (e) endothelin receptor antagonists, (f) nitric oxide donors/releasing molecules including organic nitrates/nitrites such as nitroglycerin, isosorbide dinitrate and amyl nitrite, inorganic nitroso compounds such as sodium nitroprusside, sydnonimines such as molsidomine and linsidomine, nonoates such as diazenium diolates and NO adducts of alkanediamines, S-nitroso compounds including low molecular weight compounds (e.g., S-nitroso derivatives of captopril, glutathione and N-acetyl penicillamine) and high molecular weight compounds (e.g., S-nitroso derivatives of proteins, peptides, oligosaccharides, polysaccharides, synthetic polymers/oligomers and natural polymers/oligomers), as well as C-nitroso-compounds, O-nitroso-compounds, N-nitroso-compounds and L-arginine, (g) ACE inhibitors such as cilazapril, fosinopril and enalapril, (h) ATII-receptor antagonists such as saralasin and losartin, (i) platelet adhesion inhibitors such as albumin and polyethylene oxide, (j) platelet aggregation inhibitors including cilostazole, aspirin and thienopyridine (ticlopidine, clopidogrel) and GP IIb/IIIa inhibitors such as abciximab, epitifibatide and tirofiban, (k) coagulation pathway modulators including heparinoids such as heparin, low molecular weight heparin, dextran sulfate and β-cyclodextrin tetradecasulfate, thrombin inhibitors such as hirudin, hirulog, PPACK(D-phe-L-propyl-L-arg-chloromethylketone) and argatroban, FXa inhibitors such as antistatin and TAP (tick anticoagulant peptide), Vitamin K inhibitors such as warfarin, as well as activated protein C, (l) cyclooxygenase pathway inhibitors such as aspirin, ibuprofen, flurbiprofen, indomethacin and sulfinpyrazone, (m) natural and synthetic corticosteroids such as dexamethasone, prednisolone, methprednisolone and hydrocortisone, (n) lipoxygenase pathway inhibitors such as nordihydroguairetic acid and caffeic acid, (o) leukotriene receptor antagonists, (p) antagonists of E- and P-selectins, (q) inhibitors of VCAM-1 and ICAM-1 interactions, (r) prostaglandins and analogs thereof including prostaglandins such as PGE1 and PGI2 and prostacyclin analogs such as ciprostene, epoprostenol, carbacyclin, iloprost and beraprost, (s) macrophage activation preventers including bisphosphonates, (t) HMG-CoA reductase inhibitors such as lovastatin, pravastatin, fluvastatin, simvastatin and cerivastatin, (u) fish oils and omega-3-fatty acids, (v) free-radical scavengers/antioxidants such as probucol, vitamins C and E, ebselen, trans-retinoic acid and SOD mimics, (w) agents affecting various growth factors including FGF pathway agents such as bFGF antibodies and chimeric fusion proteins, PDGF receptor antagonists such as trapidil, IGF pathway agents including somatostatin analogs such as angiopeptin and ocreotide, TGF-β pathway agents such as polyanionic agents (heparin, fucoidin), decorin, and TGF-β antibodies, EGF pathway agents such as EGF antibodies, receptor antagonists and chimeric fusion proteins, TNF-α pathway agents such as thalidomide and analogs thereof, Thromboxane A2 (TXA2) pathway modulators such as sulotroban, vapiprost, dazoxiben and ridogrel, as well as protein tyrosine kinase inhibitors such as tyrphostin, genistein and quinoxaline derivatives, (x) MMP pathway inhibitors such as marimastat, ilomastat and metastat, (y) cell motility inhibitors such as cytochalasin B, (z) antiproliferative/antineoplastic agents including antimetabolites such as purine analogs (e.g., 6-mercaptopurine or cladribine, which is a chlorinated purine nucleoside analog), pyrimidine analogs (e.g., cytarabine and 5-fluorouracil) and methotrexate, nitrogen mustards, alkyl sulfonates, ethylenimines, antibiotics (e.g., daunorubicin, doxorubicin), nitrosoureas, cisplatin, agents affecting microtubule dynamics (e.g., vinblastine, vincristine, colchicine, Epo D, paclitaxel and epothilone), caspase activators, proteasome inhibitors, angiogenesis inhibitors (e.g., endostatin, angiostatin and squalamine), rapamycin, cerivastatin, flavopiridol and suramin, (aa) matrix deposition/organization pathway inhibitors such as halofuginone or other quinazolinone derivatives and tranilast, (bb) endothelialization facilitators such as VEGF and RGD peptide, and (cc) blood rheology modulators such as pentoxifylline.

Numerous additional therapeutic agents useful for the practice of the present invention are also disclosed in U.S. Pat. No. 5,733,925 assigned to NeoRx Corporation, the entire disclosure of which is incorporated by reference.

A wide range of therapeutic agent loadings can be used in connection with the medical devices of the present invention, with the therapeutically effective amount being readily determined by those of ordinary skill in the art and ultimately depending, for example, upon the condition to be treated, the age, sex and condition of the patient, the nature of the therapeutic agent, the nature of the polymeric release region(s), the nature of the medical device, and so forth.

Numerous techniques are available for forming polymeric release regions in accordance with the present invention.

For example, where the polymeric release region is formed from one or more polymers having thermoplastic characteristics, a variety of standard thermoplastic processing techniques can be used to form the polymeric release region, including compression molding, injection molding, blow molding, spinning, vacuum forming and calendaring, as well as extrusion into sheets, fibers, rods, tubes and other cross-sectional profiles of various lengths. Using these and other thermoplastic processing techniques, entire devices or portions thereof can be made. It is noted, however, that certain polycyclic-structure-containing polymers do not even display a glass transition temperature.

In other embodiments, solvent-based techniques are used to form the polymeric release regions of the present invention. Using these techniques, a polymeric release region can be formed by providing a solution that contains the polymer(s)

that form the release region. The solvent that is ultimately selected will contain one or more solvent species, which are generally selected based on their ability to dissolve the polymer(s) that form the polymeric release region, as well as other factors, including drying rate, surface tension, etc. Generally, several solvents will be tested to see which provides polymeric release regions having the best characteristics. Preferred solvent-based techniques include, but are not limited to, solvent casting techniques, spin coating techniques, web coating techniques, solvent spraying techniques, dipping techniques, techniques involving coating via mechanical suspension including air suspension, ink jet techniques, electrostatic techniques, and combinations of these processes.

In some embodiments of the invention, a polymer containing solution (where solvent-based processing is employed) or polymer melt (where thermoplastic processing is employed) is applied to a substrate to form a polymeric release region. For example, the substrate can correspond to all or a portion of an implantable or insertable medical device to which a polymeric release region is applied. The substrate can also be, for example, a template, such as a mold, from which the polymeric release region is removed after solidification. In other embodiments, for example, extrusion and co-extrusion techniques, one or more polymeric release regions are formed without the aid of a substrate.

In a more specific example, an entire stent body is extruded. In another, a polymer release layer is co-extruded along with and underlying stent body. In another, a polymeric layer is provided on an underlying step body by spraying or extruding a coating layer onto a pre-existing stent body. In yet another more specific example, a stent is cast in a mold.

If it is desired to provide one or more therapeutic agents (and/or any other optional agents) in the polymeric release region, so long as these agents are stable under processing conditions, then they can be provided within the polymer containing solution or polymer melt and co-processed along with the polymer(s).

Alternatively, therapeutic and/or other optional agents can be introduced subsequent to the formation of the polymeric release region in some embodiments. For instance, in some embodiments, the therapeutic and/or any optional agents are dissolved or dispersed within a solvent, and the resulting solution contacted with a previously formed polymeric release region (e.g., using one or more of the application techniques described above, such as dipping, spraying, etc.).

As noted above, barrier regions are provided over therapeutic-agent-containing regions in some embodiments of the invention. In these embodiments, a polymeric barrier region can be formed over a therapeutic-agent-containing region, for example, using one of the solvent based or thermoplastic techniques described above. Alternatively, a previously formed polymeric release region can be adhered over a therapeutic agent containing region.

Although various embodiments are specifically illustrated and described herein, it will be appreciated that modifications and variations of the present invention are covered by the above teachings and are within the purview of the appended claims without departing from the spirit and intended scope of the invention.

The invention claimed is:

1. An implantable or insertable medical device comprising: (a) a polymeric release region comprising a polycyclic-structure-containing polymer which comprises a rigid, nonplanar polycyclic molecular structure; and (b) a therapeutic agent is disposed beneath or within the polymeric release region, wherein said polymeric release region controls the release of said therapeutic agent from the medical device upon implantation or insertion of said device into a subject.

2. The medical device of claim 1, wherein said polycyclic-structure-containing polymer comprises a plurality of rigid, non-planar polycyclic structures.

3. The medical device of claim 1, wherein said polycyclic-structure-containing polymer comprises a first polymer chain having a rigid, non-planar polycyclic backbone.

4. The medical device of claim 3, wherein said polycyclic-structure-containing polymer comprises a plurality of polymer chains having a rigid, non-planar polycyclic backbone.

5. The medical device of claim 3, wherein said polycyclic-structure-containing polymer is of intrinsic microporosity.

6. The medical device of claim 3, wherein said first polymer chain is formed from the polymerization of at least first and second cyclic monomers.

7. The medical device of claim 6, wherein the rings of said first and second cyclic monomers are fused to one another by means of two —O— linkages.

8. The medical device of claim 6, wherein at least one of said first and second cyclic monomers is selected from (i) polycyclic monomers having a rigid, non-planar structure, and (ii) polycyclic monomers comprising two rigid cyclic structures that are attached by a single covalent bond around which rotation between the cyclic structures is hindered.

9. The medical device of claim 6, wherein at least one of said first and second cyclic monomers is selected from

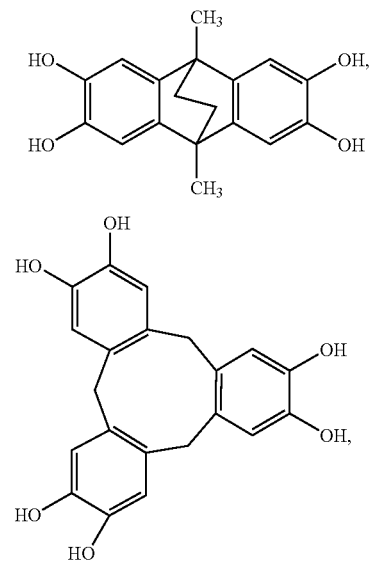

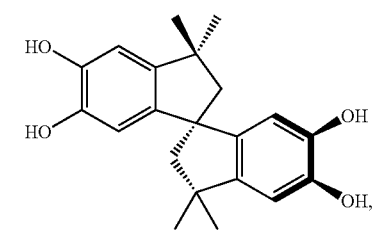

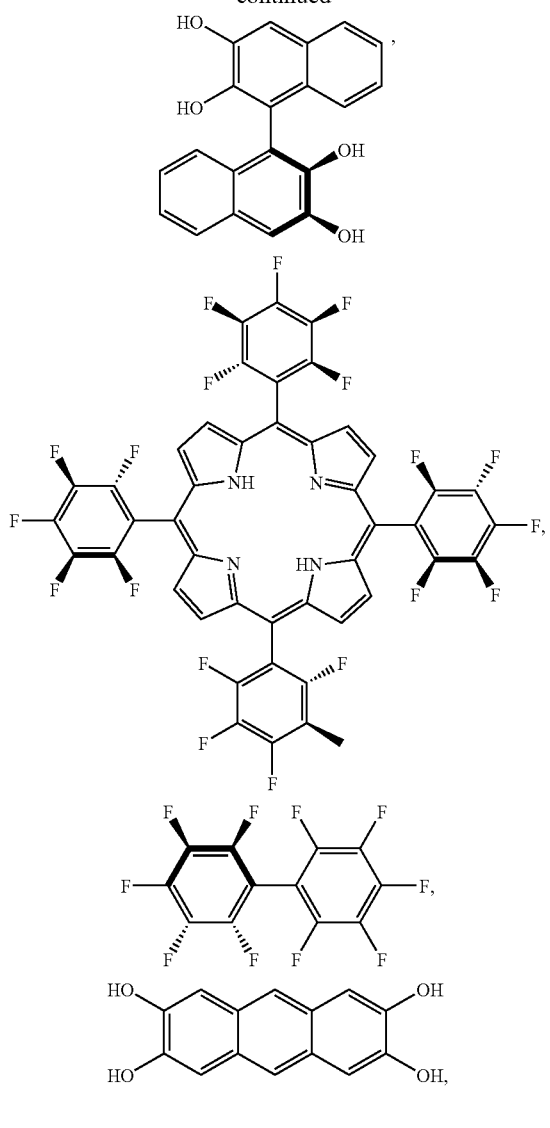

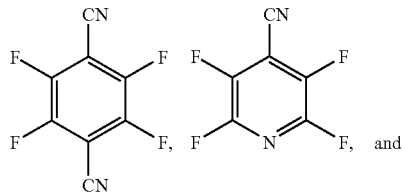

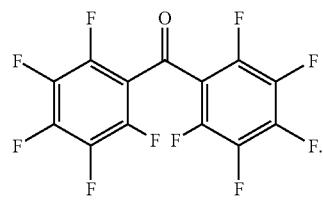

10. The medical device of claim 3, wherein said polycyclic-structure-containing polymer is a block copolymer that further comprises a second polymer chain that does not comprise a rigid, nonplanar polycyclic molecular structure.

11. The medical device of claim 10, wherein said second polymer chain is a low glass transition temperature polymer chain.

12. The medical device of claim 3, wherein said release region further comprises an additional polymer that is not a polycyclic-structure-containing polymer.

13. The medical device of claim 3, wherein said therapeutic agent is disposed beneath said release region.

14. The medical device of claim 3, wherein said therapeutic agent is disposed within said release region.

15. The medical device of claim 1, wherein said polycyclic-structure-containing polymer comprises a plurality of pendant rigid, non-planar polycyclic structures along a first polymer chain.

16. The medical device of claim 15, wherein said first polymer chain is formed from one or more monomers that comprise a rigid, non-planar polycyclic structure.

17. The medical device of claim 15, wherein said first polymer chain is formed from one or more monomers selected from

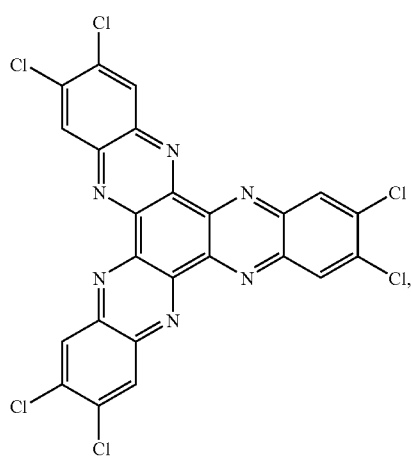

-continued

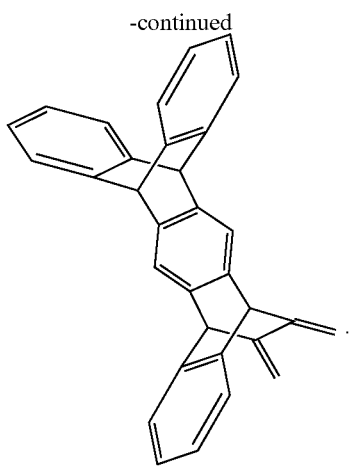

18. The medical device of claim 15, wherein said first polymer chain is formed from the copolymerization of one or more monomers that comprise a rigid, non-planar polycyclic structure and one or more monomers that do not comprise a rigid non-planar polycyclic structure.

19. The medical device of claim 18, wherein said one or more monomers that do not comprise a rigid, non-planar polycyclic structure -are selected from low Tg vinyl ether monomers, low Tg acrylate monomers, low Tg methacrylate monomers, low Tg olefin monomers, and combinations thereof.

20. The medical device of claim 15, wherein said polycyclic-structure-containing polymer is a block copolymer that further comprises a second polymer chain that does not comprise a plurality of pendant rigid, non-planar polycyclic structures.

21. The medical device of claim 20, wherein said second polymer chain is a low glass transition temperature polymer chain.

22. The medical device of claim 15, wherein said release region further comprises an additional polymer that is not a polycyclic-structure-containing polymer.

23. The medical device of claim 15, wherein said therapeutic agent is disposed beneath said release region.

24. The medical device of claim 15, wherein said therapeutic agent is disposed within said release region.

25. The medical device of claim 1, wherein said polycyclic-structure-containing polymer is a block copolymer that further comprises a polymer chain that does not comprise a rigid, non-planar polycyclic structure.

26. The medical device of claim 25, wherein said polymer chain is a low glass transition temperature polymer chain.

27. The medical device of claim 1, wherein said release region further comprises an additional polymer that is not a polycyclic-structure-containing polymer.

28. The medical device of claim 27, wherein said additional polymer comprises a low glass transition temperature chain.

29. The medical device of claim 1, wherein said therapeutic agent is disposed beneath said release region.

30. The medical device of claim 1, wherein said therapeutic agent is disposed within said release region.

31. The medical device of claim 1, wherein the polymeric release region is formed via a solvent processing method.

32. The medical device of claim 1, wherein said polymeric layer is disposed over a substrate.

* * * * *